(12) United States Patent
Krolik et al.

(10) Patent No.: US 6,969,396 B2
(45) Date of Patent: Nov. 29, 2005

(54) FILTER MEMBRANE WITH INCREASED SURFACE AREA

(75) Inventors: Jeff Krolik, Campbell, CA (US); Amr Salahieh, Saratoga, CA (US); Farhad Khosravi, San Mateo, CA (US); Richard J. Renati, Los Gatos, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/430,940

(22) Filed: May 7, 2003

(65) Prior Publication Data

US 2004/0225321 A1    Nov. 11, 2004

(51) Int. Cl.⁷ ............................................. A61M 29/00
(52) U.S. Cl. ..................................................... 606/200
(58) Field of Search ......................................... 606/200

(56) References Cited

U.S. PATENT DOCUMENTS

| | | |
|---|---|---|
| 3,472,230 A | 10/1969 | Fogarty |
| 3,952,747 A | 4/1976 | Kimmell, Jr. |
| 3,996,938 A | 12/1976 | Clark, III |
| 4,046,150 A | 9/1977 | Schwartz et al. |
| 4,425,908 A | 1/1984 | Simon |
| 4,494,531 A | 1/1985 | Gianturco |
| 4,590,938 A | 5/1986 | Segura et al. |
| 4,619,246 A | 10/1986 | Molgaard-Nielsen et al. |
| 4,643,184 A | 2/1987 | Mobin-Uddin |
| 4,650,466 A | 3/1987 | Luther |
| 4,688,553 A | 8/1987 | Metals |
| 4,706,671 A | 11/1987 | Weinrib |
| 4,723,549 A | 2/1988 | Wholey et al. |
| 4,790,812 A | 12/1988 | Hawkins, Jr. et al. |
| 4,790,813 A | 12/1988 | Kensey |
| 4,794,928 A | 1/1989 | Kletschka |
| 4,807,626 A | 2/1989 | McGirr |
| 4,842,579 A | 6/1989 | Shiber |
| 4,873,978 A | 10/1989 | Ginsburg |
| 4,921,478 A | 5/1990 | Solano et al. |
| 4,921,484 A | 5/1990 | Hillstead |
| 4,926,858 A | 5/1990 | Gifford, III et al. |
| 4,969,891 A | 11/1990 | Gewertz |
| 4,998,539 A | 3/1991 | Delsanti |
| 5,002,560 A | 3/1991 | Machold et al. |
| 5,011,488 A | 4/1991 | Ginsburg |
| 5,053,008 A | 10/1991 | Bajaj |
| 5,071,407 A | 12/1991 | Termin et al. |
| 5,100,423 A | 3/1992 | Fearnot |
| 5,102,415 A | 4/1992 | Guenther et al. |

(Continued)

FOREIGN PATENT DOCUMENTS

DE    28 21 048    7/1980

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

*Primary Examiner*—Anhtuan T. Nguyen
*Assistant Examiner*—Charles Sam
(74) *Attorney, Agent, or Firm*—Crompton, Seager & Tufte LLC (57) ABSTRACT

A filtering device with an increased surface area, and method of making and using the same. The present invention comprises a filtering device including an elongate shaft and a filter coupled to the shaft. The filter may include a filter membrane configured to have an increased surface area.

12 Claims, 6 Drawing Sheets

U.S. PATENT DOCUMENTS

| | | |
|---|---|---|
| 5,108,419 A | 4/1992 | Reger et al. |
| 5,133,733 A | 7/1992 | Rasmussen et al. |
| 5,152,771 A | 10/1992 | Sabbaghian et al. |
| 5,152,777 A | 10/1992 | Goldberg et al. |
| 5,160,342 A | 11/1992 | Reger et al. |
| 5,224,953 A | 7/1993 | Morgentaler |
| 5,329,942 A | 7/1994 | Gunther et al. |
| 5,330,484 A | 7/1994 | Gunther |
| 5,350,398 A | 9/1994 | Pavenik et al. |
| 5,354,310 A | 10/1994 | Garnie et al. |
| 5,370,657 A | 12/1994 | Irie |
| 5,376,100 A | 12/1994 | Lefebvre |
| 5,383,887 A | 1/1995 | Nadal |
| 5,421,832 A | 6/1995 | Lefebvre |
| 5,423,742 A | 6/1995 | Theron |
| 5,449,372 A | 9/1995 | Schmaltz et al. |
| 5,456,667 A | 10/1995 | Ham et al. |
| 5,462,529 A | 10/1995 | Simpson et al. |
| 5,536,242 A | 7/1996 | Willard et al. |
| 5,549,626 A | 8/1996 | Miller et al. |
| 5,601,595 A | 2/1997 | Smith |
| 5,626,605 A | 5/1997 | Irie et al. |
| 5,634,942 A | 6/1997 | Chevillon et al. |
| 5,649,953 A | 7/1997 | Lefebvre |
| 5,658,296 A | 8/1997 | Bates et al. |
| 5,662,671 A | 9/1997 | Barbut et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,728,066 A | 3/1998 | Daneshvar |
| 5,746,767 A | 5/1998 | Smith |
| 5,749,848 A | 5/1998 | Jang et al. |
| 5,769,816 A | 6/1998 | Barbut et al. |
| 5,779,716 A | 7/1998 | Cano et al. |
| 5,779,732 A | 7/1998 | Amundson |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,824,374 A | 10/1998 | Bradley, Jr. et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,895,399 A | 4/1999 | Barbut et al. |
| 5,910,154 A | 6/1999 | Tsugita et al. |
| 5,911,734 A | 6/1999 | Tsugita et al. |
| 5,925,016 A | 7/1999 | Chornenky et al. |
| 5,925,060 A | 7/1999 | Forber |
| 5,925,062 A | 7/1999 | Purdy |
| 5,928,261 A | 7/1999 | Ruiz |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,954,745 A | 9/1999 | Gertler et al. |
| 5,968,071 A | 10/1999 | Chevillon et al. |
| 5,980,555 A | 11/1999 | Barbut et al. |
| 5,984,947 A | 11/1999 | Smith |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,007,558 A | 12/1999 | Ravenscroft et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,156,373 A | 12/2000 | Zhong et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,203,732 B1 | 3/2001 | Clubb et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,325,815 B1 | 12/2001 | Kusleika et al. |
| 6,336,934 B1 | 1/2002 | Gilson et al. |
| 6,344,049 B1 | 2/2002 | Levinson et al. |
| 6,361,545 B1 * | 3/2002 | Macoviak et al. ........... 606/200 |
| 6,364,895 B1 | 4/2002 | Greenhalgh |
| 6,371,971 B1 * | 4/2002 | Tsugita et al. ............... 606/200 |
| 6,375,670 B1 | 4/2002 | Greenhalgh |
| 6,383,206 B1 * | 5/2002 | Gillick et al. ................ 606/200 |
| 6,391,044 B1 | 5/2002 | Yadav et al. |
| 6,398,756 B2 | 6/2002 | Peterson et al. |
| 6,423,086 B1 * | 7/2002 | Barbut et al. ................ 606/200 |
| 6,432,122 B1 | 8/2002 | Gilson et al. |
| 6,468,291 B2 | 10/2002 | Bates et al. |
| 6,485,502 B2 | 11/2002 | Don Michael et al. |
| 6,506,203 B1 | 1/2003 | Boyle et al. |
| 6,511,496 B1 | 1/2003 | Huter et al. |
| 6,537,294 B1 | 3/2003 | Boyle et al. |
| 6,540,768 B1 | 4/2003 | Diaz et al. |
| 6,544,279 B1 | 4/2003 | Hopkins et al. |
| 6,554,849 B1 | 4/2003 | Jones et al. |
| 6,558,405 B1 | 5/2003 | McInnes |
| 2003/0065355 A1 * | 4/2003 | Weber ........................ 606/200 |
| 2003/0074019 A1 * | 4/2003 | Gray et al. .................. 606/200 |

FOREIGN PATENT DOCUMENTS

| | | |
|---|---|---|
| DE | 34 17 738 | 11/1985 |
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1998 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/16382 | 4/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | EP 0 934 729 | 8/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01//67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |
| WO | WO 2004/019817 A1 | 3/2004 |
| WO | WO 2004/110830 A2 | 11/2004 |

OTHER PUBLICATIONS

"Endovascular Grafts, Stents Drive Interventional Radiology Growth," *Cardiovascular Device Update*, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," AJR, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," *Surgery*, 64(3):634-639 (Sep. 1968).

Haissaguerre et al., "Spontaneous Initiation of Atrial Fibrillation by Ectopic Beats Originating in the Pulmonary Veins," *The New England Journal of Medicine, 339*(10): 659-666 (Sep. 1988).

Jordan, Jr. et al., "Microemboli Detected by Transcranial Doppler Monitoring . . . ," Cardiovascular Surgery, 7(1)33-38 (Jan. 1999).

Lesh, "Can Catheter Ablation Cure Atrial Fibrillation?" *ACC Current Journal Review,* pp. 38-40 (Sep./Oct. 1997).

Lund et al., "Long-Term Patentcy of Ductus Arteriosus After Balloon Dilation: an Experimental Study," Laboratory Investigation, 69(4):772-774 (Apr. 1984).

Marache et al., "Percutaneous Transluminal Venous Angioplasty . . . ," *American Heart Journal,* 125(2 Pt 1):362-366 (Feb. 1993).

Mazur et al., "Directional Atherectomy with the Omnicath™: A Unique New Catheter System," *Catheterization and Cardiovascular Diagnosis,* 31:17-84 (1994).

Moussa, MD, Issaam "Stents Don't Require Systemic Anticoagulation . . . But the Technique (and Results) Must be Optimal," Journal of Invasive Cardiol., 8(E):3E-7E, (1996).

Nakanishi et al., "Catheter Intervention to Venous System Using Expandable Metallic Stents," Rinsho Kyobu Geka, 14(2):English Abstract Only (Apr. 1994).

Onal et al., "Primary Stenting for Complex Atherosclerotic Plaques in Aortic and Iliac Stenoses," *Cardiovascular & Interventional Radiology,* 21(5):386-392 (1998).

Theron et al., "New Triple Coaxial Catheter System for Carotid Angioplasty with Cerebral Protection," *American Journal of Neuroradiology,* 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al., "Distal Embolization is Common After Directional Atherectomy . . . ," *American Heart Journal,* 129(3):430-435 (1995).

Wholey, Mark H. et al., PTA and Stents in the Treatment of Extracranial Circulation, *The Journal of Invasive Cardiology,* 8(E):25E-30E (1996).

* cited by examiner

FILTER MEMBRANE WITH INCREASED SURFACE AREA

FIELD OF THE INVENTION

The present invention pertains to filtering devices. More particularly, the present invention pertains to embolic protection filtering devices having a filter membrane with an increased surface area.

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, embolic debris can be separated from the wall of the blood vessel. If this debris enters the circulatory system, it could block other vascular regions including the neural and pulmonary vasculature. During angioplasty procedures, stenotic debris may also break loose due to manipulation of the blood vessel. Because of this debris, a number of devices, termed embolic protection devices, have been developed to filter out this debris.

BRIEF SUMMARY

The invention provides design, material, manufacturing method, and use alternatives for intravascular filtering devices. In at least some embodiments, these filtering devices include a shaft having an embolic protection filter coupled thereto. The filter may adapted and configured to have an increased surface area or otherwise include other improvements. These and other desirable features are described in greater detail below.

DETAILED DESCRIPTION

The following description should be read with reference to the drawings wherein like reference numerals indicate like elements throughout the several views. The detailed description and drawings illustrate example embodiments of the claimed invention.

Figure 1:
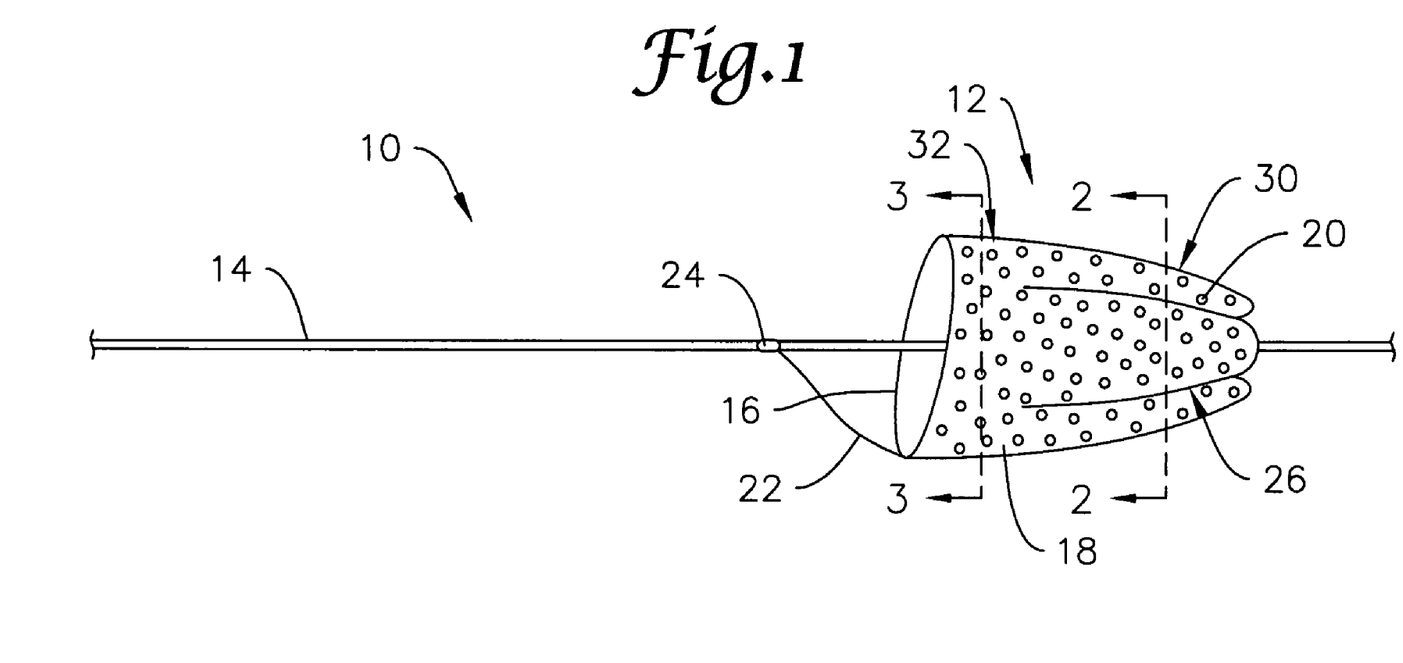
FIG. 1 is side view of an example embolic protection filtering device.

For a number of reasons, it may be desirable to augment the amount of surface area on a device that can be used for filtering debris. FIG. 1 is a side view of an example filtering device 10 including a filter 12 having an augmented surface area. This structural feature may improve the functioning of filter 12, for example, by increasing the amount of debris filter 12 can hold, by contributing to more efficient flow through filter 12, and by enhancing the strength of filter 12. It can be appreciated that the desirable structural features of filter 12 may also be described in other ways (as an alternative or in addition to having an augmented surface area) such as having an augmented filtering capability, filtering ability, filtering capacity, and the like. The augmented surface area may also provide filter 12 (and/or filtering device 10) with a number of additional desirable features including those described below.

In general, filter 12 may be adapted to operate between a first generally collapsed configuration and a second generally expanded configuration for collecting debris in a body lumen. In some embodiments, filter 12 and/or filtering device 10 can be delivered to an appropriate intravascular location, for example "downstream" of an intravascular lesion, using an appropriate filter delivery device. Similarly, filter 12 can be removed from the vasculature at the desired time by an appropriate filter retrieval device.

Filter 12 may be coupled to a shaft 14 and may include a filter frame 16 and a filter membrane or fabric 18 coupled to filter frame 16. Frame 16 may take the form of any one of a number of appropriate shapes and configurations. For example, frame 16 may comprise a generally circular filter mouth or loop, which may define the primary opening for blood to travel into and be filtered by filter 12. However, essentially any appropriate shape or configuration may be utilized without departing from the spirit of the invention.

Frame 16 may be comprised of any appropriate material. For example, frame 16 may be comprised of a "self-expanding" shape-memory material such as nickel-titanium alloy that may be configured to bias filter 12 to be in the second expanded configuration. Alternatively, frame 16 may be comprised of essentially any appropriate metal, metal-alloy, polymer, combinations thereof, and the like including any of the materials described herein. In some embodiments, frame 16 or portions thereof may be doped with, plated with, or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, plastic material loaded with a radiopaque filler, and the like. For example, a radiopaque wire disposed about a portion of frame 16.

Filter membrane 18 may be comprised of any appropriate material such as a polymer and may be drilled (for example, formed by known laser techniques) or otherwise include one or more openings 20. Holes or openings 20 can be sized to allow blood flow therethrough but restrict flow of debris or emboli floating in the body lumen or cavity. In at least some embodiments, filter membrane 18 may be configured to augment the surface area of filter 12 as is described in more detail below.

One or more struts 22 may extend between frame 16 and shaft 14. In some embodiments, struts 22 can be coupled to shaft 14 by a coupling 24, for example a heat-shrink tube, a crimp fitting, and the like. Alternatively, struts 22 may be coupled to shaft 14 by one or more windings of struts 22 about shaft 14. In some embodiments, struts 22 may comprise an extension or integral part of frame 16. Alternatively, struts 22 and frame 16 may comprise two distinct structures that can be attached to one another.

Shaft 14 can be made of any suitable materials including metals, metal alloys, polymers, or the like, or combinations or mixtures thereof. Some examples of suitable metals and metal alloys include stainless steel, such as 304v stainless steel; nickel-titanium alloy, such as nitinol, nickel-chromium alloy, nickel-chromium-iron alloy, cobalt alloy, or the like; or other suitable material. Although the embodiment shown in FIG. 1 illustrates shaft 14 as being a guidewire, shaft 14 is not intended to be limited to being only a guidewire. It can be appreciated that shaft 14 may comprise number of different structures including a catheter (e.g., therapeutic, diagnostic, or guide catheter), endoscopic device, laproscopic device, an embolic protection device, or any other suitable device. In some embodiments, shaft 14 may comprise a tubular filter cartridge. According to this embodiment, filtering device 10 (and/or shaft 14) can be configured to be slidable over a guidewire or other suitable medical device.

As stated above, filter membrane 18 may be adapted and configured to augment the surface area of filter 12. Augmenting the surface area of filter 12 may be accomplished in a number of ways. For example, filter membrane 18 may include one or more folds or pleats 26 that increase the surface area where debris may be captured or filtered. The amount of surface area that may be added to filter 12 may depend on the "depth" or amount of folding included with each pleat 26. Accordingly, the "deeper" the amount of folding included with each pleat 26, the greater the increasing in surface area. It can be appreciated that alterations to the amount of folding or depth of pleats 26 may vary without departing from the spirit of the invention.

Figure 2:
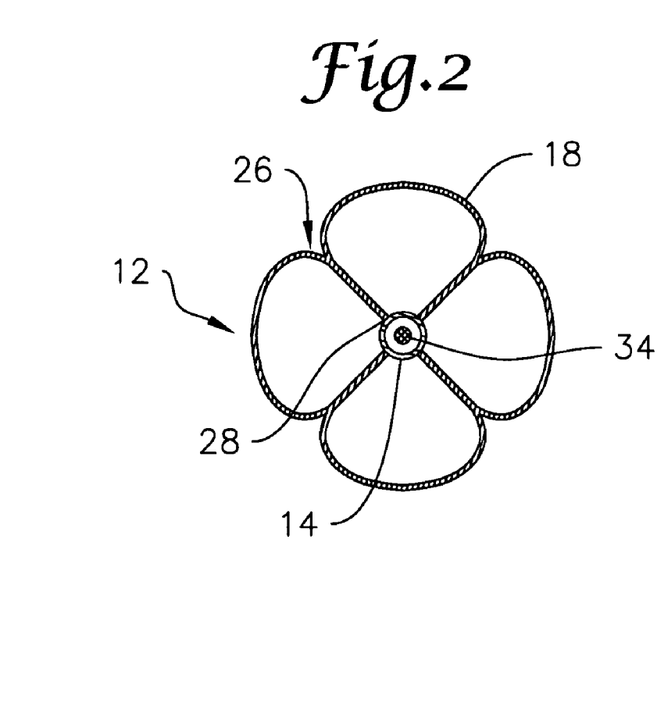
FIG. 2 is a cross-sectional view of the filtering device through line 2—2.
Figure 3:
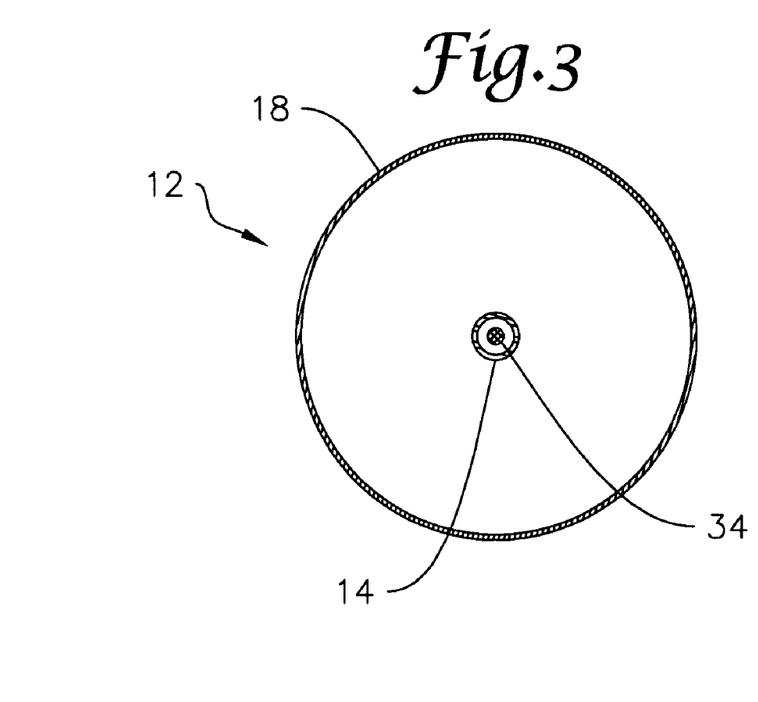
FIG. 3 is a cross-sectional view of the filtering device through line 3—3.

In at least some embodiments, pleats 26 may be defined by inward deflections of filter membrane 18. This configuration may allow filter membrane 18 to expand outwardly toward a bulbous shape when greater amounts of debris are captured. Alternatively, pleats 26 may be defined by one or more longitudinal bonds 28 between filter membrane 18 and shaft 14 as best seen in FIG. 2. Bonds 28, for example, may be disposed adjacent a distal region 30 of filter 12. Portions of filter membrane 18, however, may not be bonded to shaft 14 as best seen in FIG. 3. The non-bonded portion may be disposed adjacent a proximal region 32 of filter 12. Although the combination of FIGS. 1, 2 and 3 illustrate one example configuration of filter membrane 18 where bonds 28 are disposed along distal region 30 of filter 12 but not along proximal region 32, this arrangement is not intended to be limiting. Generally, bonds 28 may be disposed along distal region 30, along proximal region 32, along the entire length of filter 12, or any other suitable combination or arrangement. FIGS. 2 and 3 also illustrate more clearly that shaft 14 may comprise a tubular filter cartridge that may be slidable over a medical device such as a guidewire 34.

Figure 4:
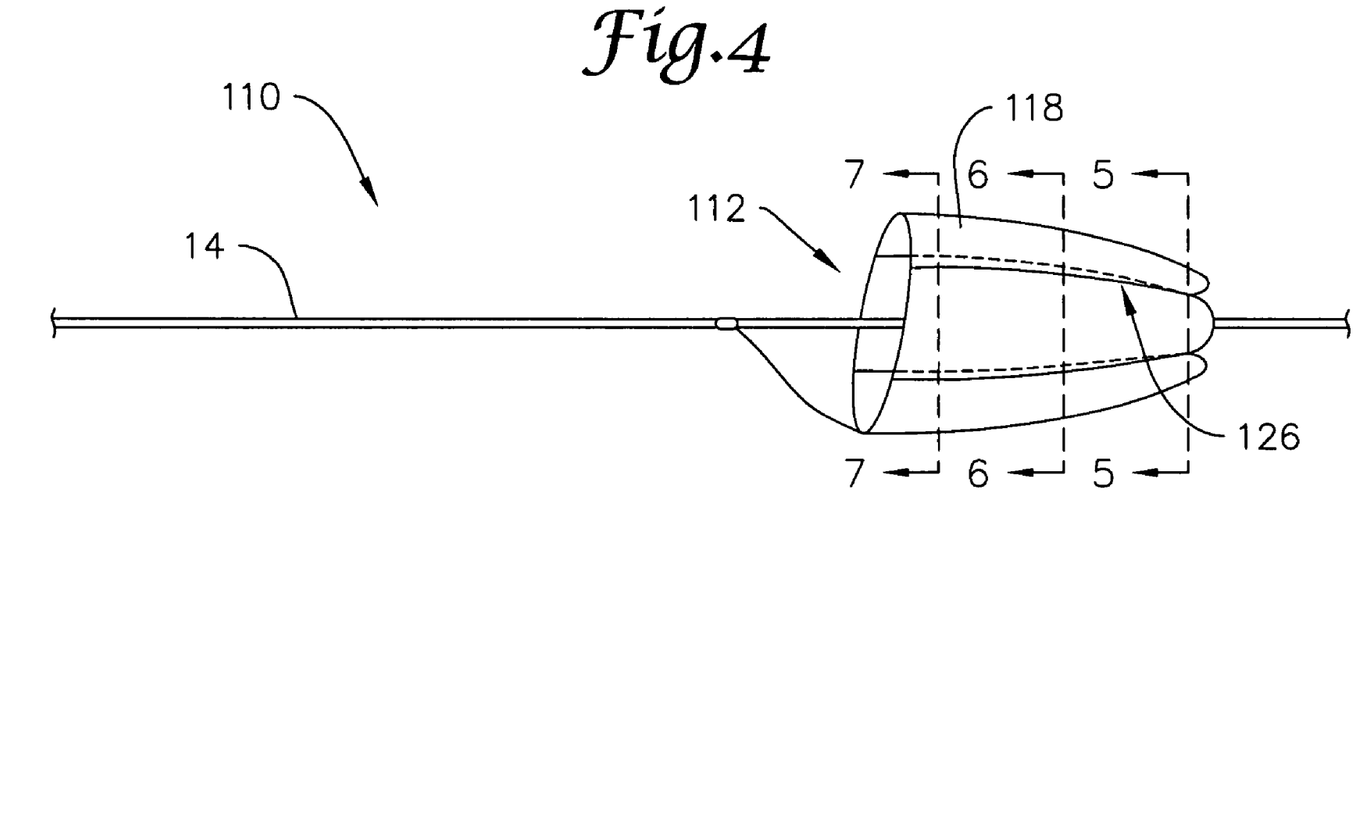
FIG. 4 is side view of another example embolic protection filtering device.

FIG. 4 is another example filtering device 110 that is essentially the same in form and function as device 10, except that filter 112 include one or more longitudinal fibers 136 (best seen in FIGS. 5, 6, and 7) and that the folds or pleats 126 of filter membrane 118 may be defined by bonds 128 (best seen in FIGS. 5, 6, and 7) between filter membrane 118 and fibers 136. According to this embodiment, fibers 136 may act as a substrate or bonding surface for filter membrane 118 as well as help define a configuration of filter 112 that has increased surface area. Fibers 136 may also provide filter 112 with other desirable features such as strength, radiopacity, etc.

Figure 5:
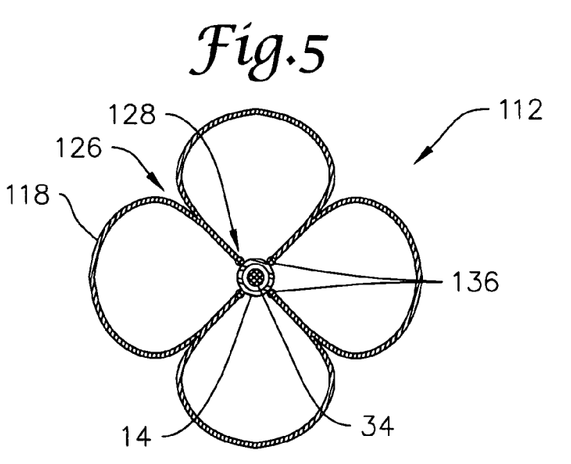
FIG. 5 is a cross-sectional view of the filtering device through line 5—5.
Figure 6:
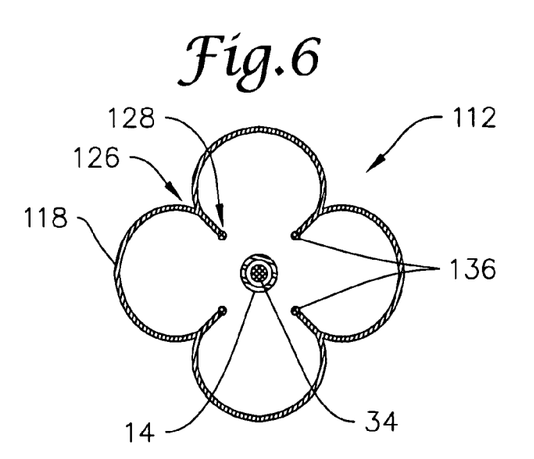
FIG. 6 is a cross-sectional view of the filtering device through line 6—6.
Figure 7:
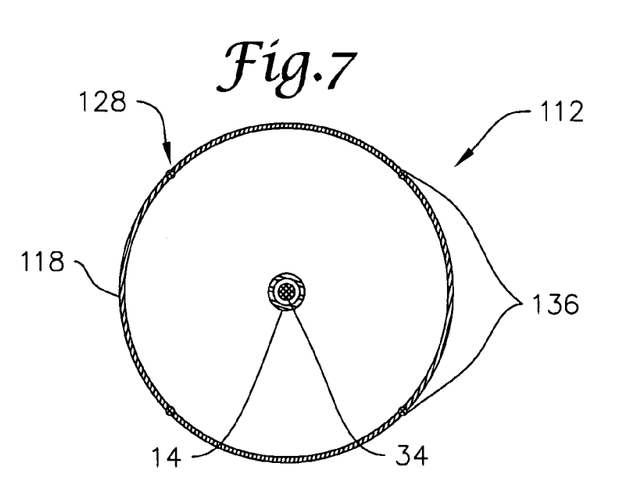
FIG. 7 is a cross-sectional view of the filtering device through line 7—7.

In at least some embodiments, fibers 136 may be attached to and extend distally from filter frame 116. For example, opposite ends of fibers 136 may be attached to filter frame 116 and shaft 14. According to this embodiment, the spacing between fibers 136 and shaft 14 gets larger at more proximal filter locations. For example, FIG. 5 is a cross-sectional view of filter 112 at a relatively distal position, illustrating fibers 136 disposed adjacent shaft 14. FIGS. 6 and 7, which illustrate increasingly more proximal positions along filter 112, depict increasing radial spacing of fibers 136 from shaft 12.

Figure 8:
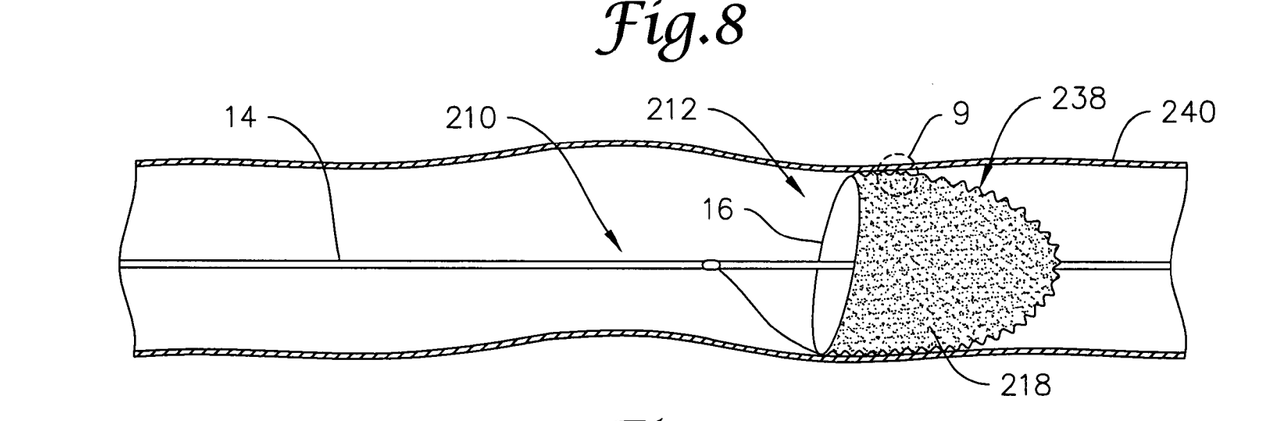
FIG. 8 is a side view of another example embolic protection filtering device.
Figure 9:
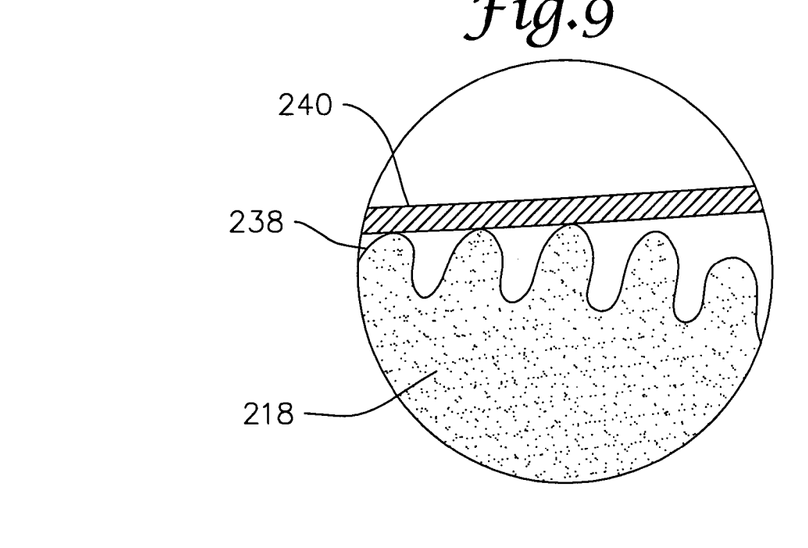
FIG. 9 is a side view of a portion of the filtering device shown in FIG. 8.

FIG. 8 is another example filtering device 210 that is essentially the same in form and function as any of the others described herein except that filter 212 includes one or more sinusoidal ribs 238. In at least some embodiments, sinusoidal ribs 238 may be attached to or disposed adjacent to filter frame 16 and/or filter membrane 18, and may extend distally along filter 212. The precise location and length of ribs 238, however, may vary. In general, ribs 238 may be configured for being disposed along the region of filter 212 that contacts or may contact the interior wall of a blood vessel 240 as shown in FIG. 9. This feature may be desirable, for example, because it allows a smaller portion of filter membrane 218 to be "blocked" by contact with blood vessel 240. Accordingly, the surface area of filter 212 that can be used to collect debris is increased.

Figure 10:
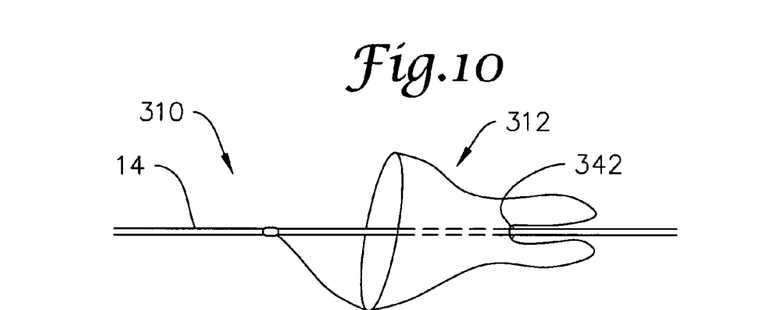
FIG. 10 is a side view of another example embolic protection filtering device.
Figure 11:
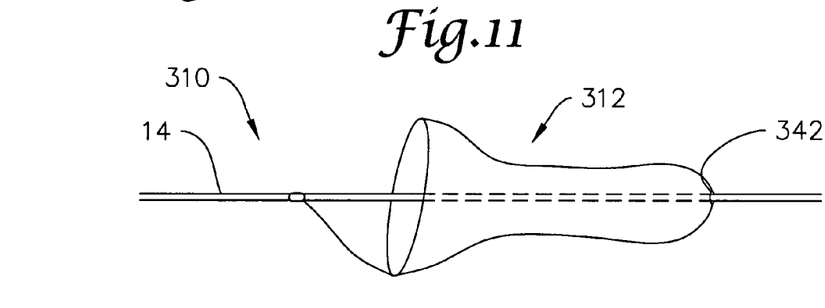
FIG. 11 is a side view of another configuration of the filtering device shown in FIG. 10.

Another example filtering device 310 is shown in FIG. 10. Device 310 is essentially the same in form and function as any of the other devices described herein except that filter 310 includes a distal apex ring member 342 that is slidable along shaft 14. Accordingly, filter 312 may be able to shift from a first relatively shortened or inverted configuration (as shown in FIG. 10) to a second relatively elongated or everted configuration (as shown in FIG. 11).

Shifting between the first and second configurations may be accomplished in a number of ways. For example, filter 312 may be originally placed within a body lumen in the first configuration and then shift to the second configuration as filter 312 becomes filled with debris. According to this embodiment, ring member 342 may frictionally engage shaft 14. However, when filter 312 becomes sufficiently full, forces exerted on filter 312 (e.g., due to fluid flow within the body lumen) may overcome the frictional force and shift filter 312 to the second configuration.

Figure 12:
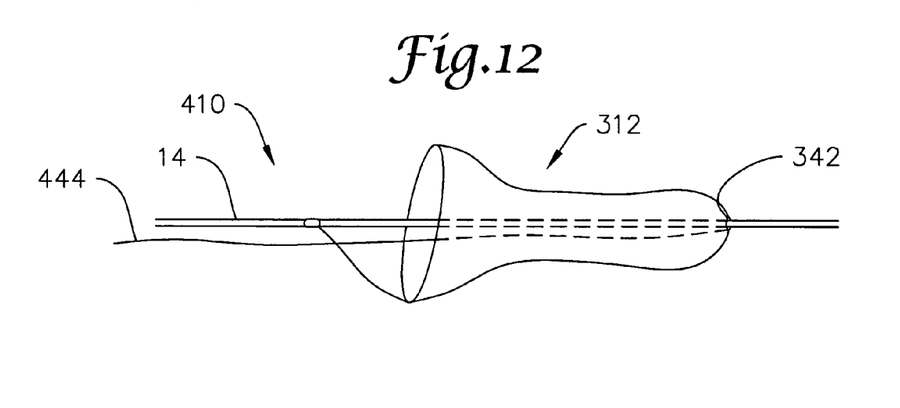
FIG. 12 is a side view of another example embolic protection filtering device.

Alternatively, shifting the configuration of filter 312 may be accomplished in another example filtering device 410 by using a shifting member or rod 444 as shown in FIG. 12. According to this embodiment, rod 444 may be attached to ring member 342 and extend proximally therefrom. A clinician may then grasp rod 444 and alter the configuration of filter 312 by proximally or distally shifting rod 444.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. An embolic protection filtering device, comprising:
    an elongate shaft having a proximal end and a distal end;
    a filter coupled to the shaft, the filter including a filter frame, and a filter membrane coupled to the filter frame; and
    the filter membrane and the filter frame expandable between a collapsed position and an expanded position, in the expanded position, the filter membrane has a proximal region and a distal region, the proximal region defining a generally smooth sided open filter mouth and the distal region includes including one or more pleats, wherein the pleats are defined by one or more bonds between the filter membrane and the shaft.

2. The filtering device of claim 1, wherein the shaft comprises a guidewire.

3. The filtering device of claim 1, wherein the shaft comprises a tubular filter cartridge configured to be slidable over a guidewire.

4. The filtering device of claim 1, wherein the filter includes a proximal region and a distal region, and wherein the pleats are disposed at the distal region.

5. The filtering device of claim 1, wherein the pleats are defined by inward deflections of the filter membrane.

6. The filtering device of claim 1, further comprising one or more support fibers extending from the filter frame to a distal end of the filter.

7. The filtering device of claim 6, wherein the pleats are defined by one or more bonds between the filter membrane and the support fibers.

8. A medical device, comprising:
    an elongate shaft having a proximal region and a distal region;
    a filter coupled to the shaft adjacent the distal region;
    the filter including a filter hoop, one or more struts extending between the filter hoop and the shaft, and a filter membrane coupled to the filter hoop and extending distally therefrom; and
    the filter membrane including a proximal region and a pleated distal region, wherein the pleated distal region is defined by one or more longitudinal bonds between the filter membrane and the elongate shaft, the pleated distal region being configured to augment the surface area of the filter.

9. The medical device of claim 8, wherein the shaft is a guidewire.

10. The medical device of claim 8, wherein the shaft comprises a tube configured to be slidably disposed over a guidewire.

11. The medical device of claim 8, further comprising one or more support fibers extending from the filter hoop to a distal apex of the filter.

12. The medical device of claim 11, wherein the filter membrane is coupled to the support fibers.

* * * * *

UNITED STATES PATENT AND TRADEMARK OFFICE
CERTIFICATE OF CORRECTION

| | | |
|---|---|---|
| PATENT NO. | : 6,969,396 B2 | Page 1 of 1 |
| APPLICATION NO. | : 10/430940 | |
| DATED | : November 29, 2005 | |
| INVENTOR(S) | : Jeff Krolik et al. | |

It is certified that error appears in the above-identified patent and that said Letters Patent is hereby corrected as shown below:

Col. 5
Claim 1, line 23, delete "including"

Signed and Sealed this

Twenty-sixth Day of December, 2006

JON W. DUDAS
*Director of the United States Patent and Trademark Office*